United States Patent [19]

Santini

[11] Patent Number: 5,060,858

[45] Date of Patent: Oct. 29, 1991

[54] METHOD AND APPARATUS FOR DISPENSING VOLATILE COMPONENTS OF AN AIR TREATING GEL

[75] Inventor: Thomas F. Santini, Allentown, N.J.

[73] Assignee: Wessel Fragrances, Inc., Elmwood Park, N.J.

[21] Appl. No.: 523,881

[22] Filed: May 14, 1990

[51] Int. Cl.⁵ ............................................. A61L 9/04
[52] U.S. Cl. ......................................... 239/60; 239/6; 239/57
[58] Field of Search ................. 239/54, 55, 56, 60, 239/57, 6; 424/76.3, 76.4; 285/297, 298

[56] References Cited

U.S. PATENT DOCUMENTS

| | | | |
|---|---|---|---|
| 1,931,132 | 10/1933 | Hinckley | 239/57 |
| 2,878,060 | 3/1959 | Russo . | |
| 3,239,145 | 3/1966 | Russo . | |
| 3,587,968 | 6/1971 | Hennart et al. . | |
| 3,908,906 | 9/1975 | Crowle et al. | 239/60 |
| 3,910,495 | 10/1975 | Cummings et al. | 239/60 |
| 4,157,787 | 6/1979 | Schwartz . | |
| 4,755,377 | 7/1988 | Steer . | |
| 4,809,912 | 3/1989 | Santini . | |

Primary Examiner—Andres Kashnikow
Assistant Examiner—Christopher G. Trainor
Attorney, Agent, or Firm—Davis, Bujold & Streck

[57] ABSTRACT

A dispenser for dispensing volatile products present in a gel in which the gel is anchored to the dispenser throughout the perimeter of an emanating surface of the gel from which the volatile products are dispensed. The emanating surface is replenished from a reservoir of gel within the dispenser while the emanating surface remains substantially stable and free of shrinkage as a result of its anchorage to the container. The anchoring means may be a porous material or appropriately shaped flanges and openings adjacent the emanating surface in the structure of the dispenser.

11 Claims, 3 Drawing Sheets

METHOD AND APPARATUS FOR DISPENSING VOLATILE COMPONENTS OF AN AIR TREATING GEL

This invention relates to dispensing devices and more particularly to dispensing devices and methods for controlled release of air treating materials from a device that uses a gel reservoir. The invention has particular application for use with so-called continuous action air freshening units and will be described in connection with such application although other applications are contemplated.

The controlled dispensing of fragrance and the capacity to create an odor impression in a substantially closed space is the primary concern of all the methodologies which have addressed the area of air freshening and fragrance diffusion. The importance of a controlled release not only manifests itself from the point of view of fragrance selection, but also proves to be important when concern over the functional life of the unit is considered. Economically viable devices must be efficient in their performance due to high costs often associated with fragrance. Premature release of the fragrance not only creates a potential for excess odor production in the early stages of the product's functional life, but also diminishes the reservoir of fragrance which can be drawn upon in the latter stages of the performance life of the device. Diffusion methodologies are frequently compared over a given time frame with identical loadings of fragrance so that critical, controlled evaluations may be made with regard to odor intensity and product longevity. Superior technologies will be those that are able to produce a greater odor impression over a longer period for a given fragrance loading than similarly intended methodologies.

Solid compositions in which a fragrance or perfume is dispersed within a matrix formed by a gelling agent offer a particularly desirable and relatively low cost commercial delivery method for continuous action fragrance release devices. Gels can commonly range from being very soft solids to what is termed "ringing gels", which have greater mechanical integrity.

Typically the gel base comprises by weight of said substrate from about 0.5 to about 10% of a gel-forming agent, on an anhydrous basis; water in an amount effective to subsequently hydrate said gel-forming agent; and from about 0.2 to about 5% of said perfume constituent. Suitable gel-forming agents include carrageenan, algins, agars, and other carbohydrates such as amylose, and sodium carboxymethylcellulose.

The compositions preferably include up to about 5% of a viscosity control agent, and may further include as other optional constituents gelling aids such as potassium chloride, humectants, perfume fixatives, extenders, preservatives, freeze-thaw stabilizers, and dye.

Air treating gels provide an effective means for the gradual introduction into the air of volatilizable air treating components, including for example, air freshening and odor counteractant components. In commercial use of such gels, it has generally been the practice to prefashion bodies or slugs of gels having a suitable shape and contour, and then place the preformed bodies in a desired container or dispenser.

The prior art is replete with designs of dispensers for dispensing the volatile components of such gels with designs varying from simple housings for slugs of gel, within which the slug is allowed to deform at will during the dispensing operation with the housing not only being designed to support the slug, often with means for attachment to a desired surface, and to visually obscure the slug as it deforms in what is usually not a very aesthetically pleasing manner, to relatively expensive designs involving a multiplicity of close tolerance parts designed to control dispensation and activation of the dispenser using various mechanisms including penetrable diaphragms and selective filter membranes designed to permit transmission of evaporated volatile components of the gel only.

The closest prior art to the present invention is the use of a simple open topped container for a gel carrying volatile components which are dispensed to the air from the exposed surface of the gel through the open top of the container. While such an arrangement is economical to produce the product is not very attractive because as the volatile components are allowed to evaporate the gel will shrink toward the bottom of the container, draw away from the side walls and crack in an unattractive manner. In addition with such arrangements it is frequently not possible to readily determine when the supply of volatile material is exhausted. Additionally, the shrinkage of the gel in such container provides a varying dispensing surface and results in a substantially uncontrolled variation in dispensation of the volatile components.

A variation of this simple container is found in U.S. Pat. No. 4,157,787 in which the containers open top is covered by a layer of porous material.

It is an object of the present invention to provide a method and apparatus by the use of which a simple inexpensive open topped container may be used for the dispensation of the volatile components of the gel into the air from a surface of substantially constant area without significant visual signs of shrinkage of the gel apparent in this gel surface yet with a clear indication as to when the volatile components of the gel are about to be or have been exhausted.

It is a further object of the present invention to provide such method and apparatus in which the dispenser is easily filled during manufacture and is sealed hermetically until dispensation of the volatile components of the gel contained therein is desired.

According to the invention there is provided a dispenser for dispensing volatile products by evaporation from an emanating surface of a gel, comprising an open topped container defining an opening from which the volatile products may be dispensed from said container having attachment means, disposed within the container adjacent the opening around the entire perimeter thereof, for purposes of anchoring the gel adjacent said opening to the container to define an emanating surface of the gel adjacent the opening whereby during use, shrinkage of the gel will occur within the container as the gel within the container acts as a reservoir supplying the stationary emanating surface.

Also according to the invention there is provided a process for providing a stable emanating surface of gel for the dispensation of volatile products therefrom comprising anchoring the gel to a structure surrounding the emanating surface and providing a reservoir of gel to replenish the emanating surface as volatile products are dispensed.

The invention will now be described, by way of example, with reference to the accompanying drawings, in which.

Figure 1:
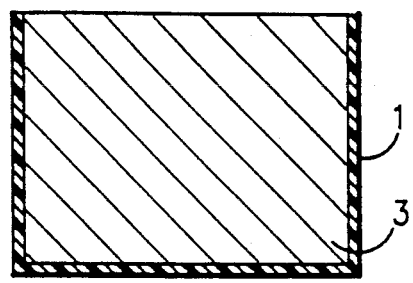
FIG. 1 is a diagrammatic cross-section of a prior art open topped container dispenser immediately after the surface of gel therein has been exposed to the air for dispensation of volatile components thereof.
Figure 2:
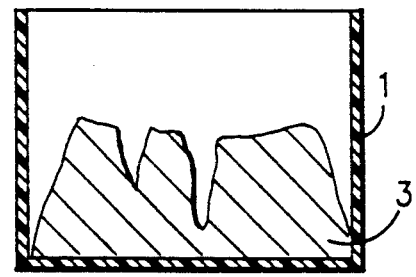
FIG. 2 is a diagrammatic cross-section of the prior art dispenser of FIG. 1 after the period of use illustrating the shrinkage of the gel from the walls of the container and the cracking of the gel with the resulting changes in dispensing surface area and with the resulting unattractive appearance of the gel.
Figure 3:
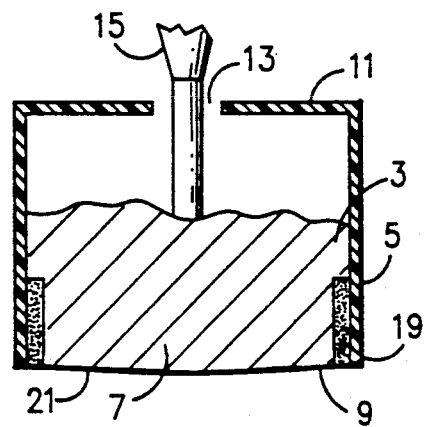
FIG. 3 is a diagrammatic cross-section of a dispenser according to the present invention shown inverted in the process of being filled.
Figure 4:
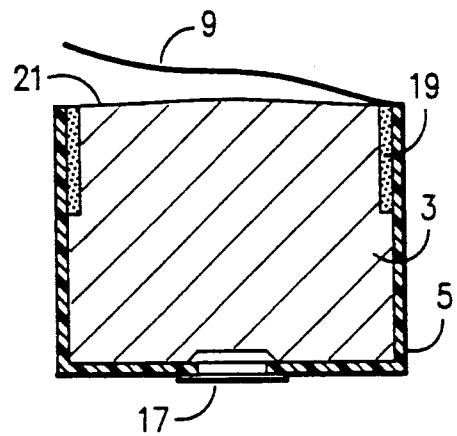
FIG. 4 is a diagrammatic cross-section of the dispenser of FIG. 3 after being filled shown upright at the time of activation to commence the dispensation of volatile components therefrom.

With reference first to prior art FIGS. 1 and 2, an open topped container 1 shown filled with a fragrance dispensing gel 3 (FIG. 1) and after fragrance has been dispensed for a period of time (FIG. 2) with the unsightly and changing dispensing area resulting from shrinkage from the walls of the container and the cracking of the gel.

Now with reference to the present invention reference is first made to FIGS. 3 through 6. A wide mouth plastic cylindrical container 5 defines a circular opening covered, prior to filling and activation, by an impervious plastic sheet 9 sealing by engagement with the perimeter of the opening 7. It will be appreciated that the plastic sheet 9 could be replaced by a domed cap sealingly attached to the container 5, the cap being removable to activate the dispenser. The bottom 11 of the container defines a filling aperture 13 through which gel composition 3, which has been heated until liquified, is poured from a nozzle 15 (FIG. 3) to fill the container. The filling aperture 13 is sealingly closed by a plug 17 once the container is filled and in the inverted position shown in FIG. 3. Inside the container 5 adjacent the perimeter of opening is an open celled porous polyethylene band 19 fixedly attached to the container. It will be appreciated that this band may be, for example, fixed by adhesive, welded, molded in during the molding of the container or may even be a porous portion of the container material itself. The only requirement is that the band 19 act in use as a integral part of the container. The band has a width sufficient to provide the desired attachment of the gel without fear of separation of the gel from the band as it seeks to shrink during operation and insufficient to prevent the gel in the lower portion of the container from being drawn to the emanating surface 21. A width of about 15 to 30% of the diameter of the opening and/or about 20 to 40% of the height of the container is appropriate. Upon the filling of the container 5 with the liquified gel, that gel penetrates the interstices of the band 19 and upon setting becomes anchored to that band. Following the setting of that gel and the positioning of the plug 17 in the filling aperture 13 the dispensing unit is ready for packaging and distribution without loss of volatile components of the gel prior to activation of the dispenser.

The band 19 provides an attachment for the gel so that the emanating surface 21 of the gel, during operation of the dispenser remains intact, stable and in close proximity to the top of the container. This is in contrast to the natural tendency of the gel which is to shrink dimensionally in all directions. Without the benefit of the attachment to the band the gel would shrink and collapse within the confines of the container. The band, by providing attachment for the upper most portion of the gel, allows the gel, which is not affixed to the band, to act as a reservoir as it continually feeds the emanating surface and, at the same time, shrinks in the process. However, the shrinkage takes place within the confines of the container and causes virtually no change in the surface area of the emanating surface in distinct contrast to the commercially available units in which the fully exposed gel shrinks in a very unattractive manner. The band, due to the attachment it provides, allows the use of the dispenser in either the upright orientation, illustrated in FIGS. 4, 5 and 6, the inverted position shown in FIG. 3 or any other desired orientation, for example attached to a wall by the base of the container. It will be appreciated that, apart from its attachment to the band 19, the gel does not attach itself to the interior surface of the container and is thus free to act as a reservoir to replenish the emanating surface. The flexible plastic sheet 9 will deform upon the filling of the unit to define an emanating surface which in the first instance is domed so that any slight shrinkage which might occur initially in the emanating surface upon activation will result in a substantially flat surface (FIG. 5) which is substantially flush with the perimeter of the opening 7. It will be appreciated that this flat surface might further shrink slightly to form a slight concavity but that the domed shape formed in the initial filling will minimize the extent to which this concavity forms.

Figure 5:
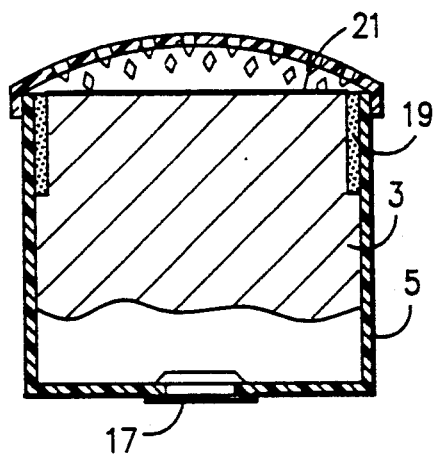
FIG. 5 is a diagrammatic cross-section of the dispenser shown in FIG. 4 after a period of time has elapsed during which volatile components have been dispensed from the gel in the container, this figure additionally illustrates a perforated cover for the container.
Figure 6:
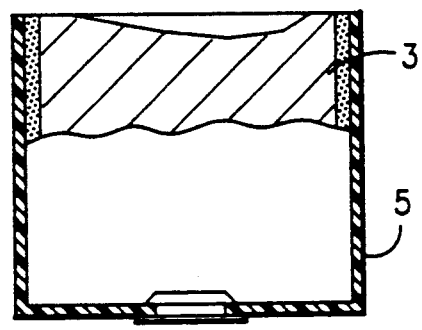
FIG. 6 is a diagrammatic cross-section of the dispenser of FIG. 4 shown when the volatile components of the gel are substantially exhausted.
Figure 7:
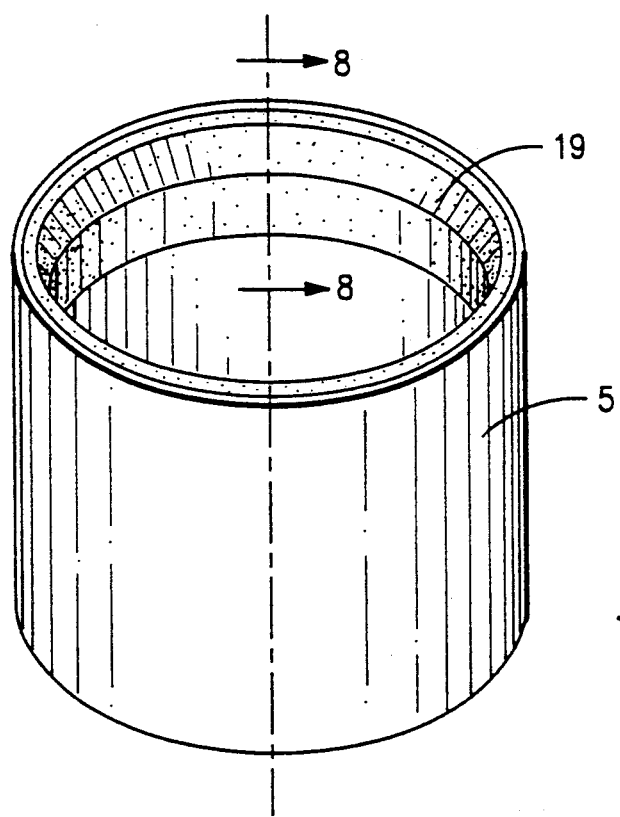
FIG. 7 is a perspective view of a dispenser according to FIG. 4 shown empty prior to filling.

To activate the dispenser, the plastic sheet 9 is peeled away from the opening (FIG. 4) thus exposing the emanating surface of the gel. The volatile components of the gel can now evaporate from the emanating surface into the surrounding air with any initial shrinkage of the emanating surface contributing to produce the substantially flat surface shown in FIG. 5. As the volatile components continue to evaporate from the surface, the gel shrinks from the bottom 11 of the container to continually supply the emanating surface with the volatile components for dispensation. A decorative cover with openings is shown in FIG. 5 and this may optionally be provided for decorative purposes, although it is not necessary or even preferable in the operation of the dispenser of this invention. As the gel becomes exhausted the gel will shrink starting from the bottom of the container and continually diminish in size as the volatile components evaporate through the surface of the gel which is exposed to the air. Once all of the volatile components have been depleted the non-volatile portion of said gel composition will come to the reside within the confines of the absorbent band (FIG. 6). In a transparent plastic housing in which the absorbent attachment band 19 is opague, the unit from a side perspective will appear empty and thus a clear indication that replacement is necessary.

Figure 9:
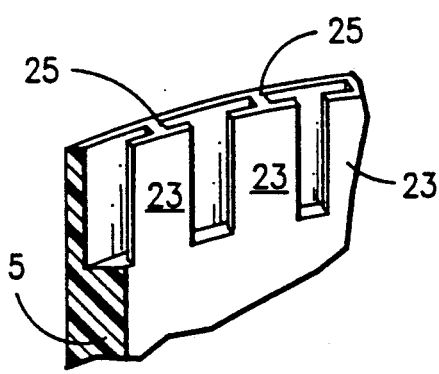
FIG. 9 is a fragmentary perspective view of the portion adjacent the opening of an alternative embodiment to the dispenser shown in FIG. 4.

The band 19 is preferably a semi-rigid porous material such as porous polyethylene adhesively attached to the inside of the container adjacent the opening 7. However, it will be appreciated that other porous materials such as a non-woven, woven and felted fabrics as well as foamed polymeric materials can be used in place of the porous plastic as could a band having a plurality of loops projecting therefrom. Alternative constructions of the container providing means for attachment of the gel to the container adjacent the opening are shown, by way of example, in FIGS. 9, 10, and 11. In FIG. 9 a plurality of circumferentially spaced longitudinally extending flanges 23 are provided with openings there behind which will hold the gel captive, once set. The circumferential flanges 23 may be attached to the exterior wall of the container 5 by webs 25, although these webs 25 are not essential. The webs, it will be appreciated, need not be of rectangular cross-section as shown but could be of any other cross-section including webs with curved walls and conical cross sections to minimize the amount of gel held captive behind the flanges 23 without destroying the integrity of the attachment.

Figure 10:
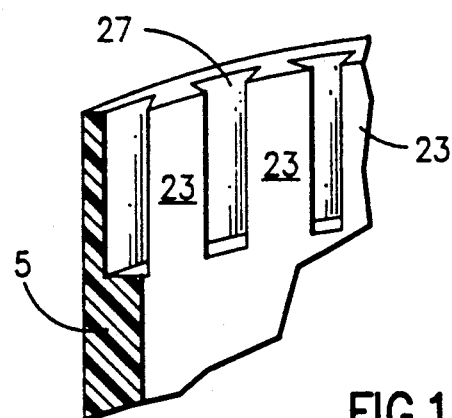
FIG. 10 is a view similar to that of FIG. 8 of a further alternative embodiment.

A variation of this is shown in FIG. 10 in which the flanges 23 are of frusto-conical cross-section with the smallest width being integral with the wall of the container 5 to form dove tail openings 27 extending longitudinally of the container from the opening toward the base 11. The longitudinal length of the flanges 23, as with the porous band, is sufficient to provide the necessary attachment of the gel to the container adjacent the opening 7 while allowing the gel between the flanges and the base 11 freedom to shrink from the container to supply the emanating surface.

Figure 11:
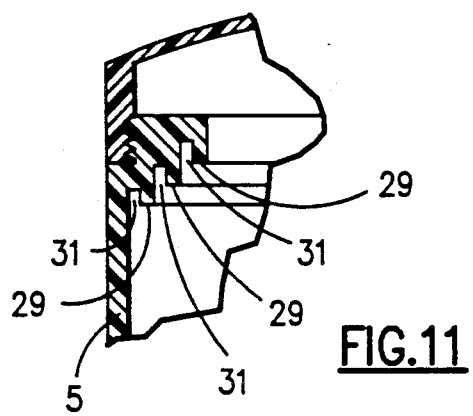
FIG. 11 is fragmentary cross-section of a portion of yet further alternative embodiment of the dispenser shown in FIG. 4.

A further embodiment is shown in FIG. 11 in which a plurality of annular flanges 29 extend from the opening longitudinally toward the base 11 to define therebehind annular cavities 31 to provide the desired attachment of the gel in this area of the container to that container. In this embodiment, a threaded exterior portion is provided adjacent the opening 7 for attachment of a decorative cover, such as that illustrated in FIG. 5.

Figure 8:
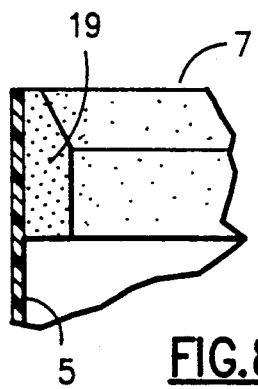
FIG. 8 is a fragmentary perspective view of the portion of the dispenser of FIG. 4 adjacent the opening thereof on section line 8—8.

While the band of porous plastic described with reference to FIGS. 3, 4, 5 and 6 may be rectangular in cross-section, one variation is to provide a tapered portion adjacently opening 7 (see FIG. 8) to increase the area of the emanating surface.

The dispenser of this invention is suitable for use, for example, in applications involving carrageenan type air freshening gel compositions (examplified hereinafter by formula 1) and metallic stearate gel compositions (examplified hereinafter as formula 2).

| Formula 1 | |
|---|---|
| Ingredients | Percent (by weight) |
| Gelling Agent | 1.7 |
| *Colloid 878 (TIC Gums, Inc.) | |
| Co-Solvents/Solubilizers | |
| Propylene Glycol | 3.0 |

-continued

| Formula 1 | |
|---|---|
| Ingredients | Percent (by weight) |
| Polyethylene Glycol E-400 | 4.0 |
| Dipropylene Glycol Methyl Ether | 9.0 |
| Sodium Stearate | 1.0 |
| Air Treating Agents | |
| Fragrance Oil | 3.5 |
| SD Alcholol 40 (95%) | 3.0 |
| Preservative | 0.1 |
| Kathon CG (Rohm & Haas Co.) | |
| Aqueous Medium | 74.7 |
| Water | |
| | 100.0 |

*Colloid 878 is a dry blended mixture of carrageenan, guar gum and salt.

The term "carrageenan" is used herein to denote a sulfate polysaccharide. The sulfated polysaccharides of the present invention are well known to the prior art and detailed discussions concerning their use in air freshener applications can be found in U.S. Pat. Nos. 4,056,612; 2,927,055 and Canadian Pat. No. 895,825.

| Formula 2 | |
|---|---|
| Ingredients | Percent (by weight) |
| Gelling Agent | 5.0 |
| Sodium Stearate | |
| Co-Solvents/Solubilizers | |
| Propylene Glycol | 10.0 |
| Diethylene Glycol Methyl Ether | 30.0 |
| Air Treating Agents | |
| Fragrance Oil | 3.0 |
| SD Alcohol 40 (95%) | 10.0 |
| Aqueous Medium | 42.0 |
| Water | |
| | 100.0 |

A further discussion of metallic stearate air freshening gels can be found in the British Patent No. 1,517,967.

It will be appreciated that the dispenser of the present invention is not limited to the use of these compositions and that it could be readily adapted to any air treating gel which is filled in a liquid state and which upon setting becomes solidified.

Apart from providing a constant emanating surface area, the arrangement of the present invention ensures that the emanating surface is exposed to any ambient air currents which help create a more perceptible odor awareness in a closed environment.

The functional aspects of the dispenser of the present invention, namely its functional life and odor intensity, are functions of the size of the reservoir, fragrance loading in the gel and the area of the emanating surface. These variables can be chosen to create a unit with a functional life of from 1 to 6 weeks, or even more, and suited for dispensing air treating agents in either a small space or a whole room. The dispenser may be of a relatively small size due to the concentrated formulation which utilizes a fragrance concentration of 3.5% as opposed to typical air freshening gels which have only a 1% fragrance load. Accordingly, the dispenser can deliver the same amount of fragrance from a somewhat smaller reservoir.

I claim:

1. A dispenser for dispensing volatile products by evaporation from a fully exposed emanating surface of a gel, comprising an open topped container having a perimeter defining an unobstructed opening from which the volatile products may be dispensed, said container having an annular attachment means, defining a plurality of interstices, disposed within the container adjacent the opening around the entire said perimeter thereof, said attachment means interstitially anchoring the gel around and adjacent said unobstructed opening of the container to define and sustain the emanating surface of the gel adjacent to the opening throughout the useful life of the dispenser, whereby during use, shrinkage of the gel will occur within the container as the gel within the container acts as a reservoir supplying the emanating surface wherein the attachment means is a band of porous material into the interstices of which liquified gel, entering the dispenser, can penetrate to form the desired anchoring of the gel once it has set.

2. A dispenser according to claim 1 further comprising an impervious membrane sealingly engaging the container about the perimeter of the opening to hermetically seal the container prior to use to dispense the volatile products.

3. A dispenser according to claim 1 wherein the container includes a wall portion defining the opening and a base closure including a filling aperture through which the liquified gel may enter the dispenser, a closure plug, for sealingly closing the aperture, being provided to sealingly close that aperture once a desired quantity of the gel has been placed in the dispenser.

4. A dispenser according to claim 2 in which the membrane is shaped to define a domed emanating surface in the gel received in the dispenser while the dispenser is in an inverted orientation.

5. A dispenser according to claim 1 wherein the porous material is one of open celled foam, woven fabric, non-woven fabric, felted textile, porous plastic, a fabric with a plurality of loops extending from a surface thereof, or a porous portion of the material of the container.

6. A dispenser according to claim 1 comprising a perforated decorative cover disposed in spaced relationship to and over said fully exposed emanating surface.

7. A dispenser for dispensing volatile products by evaporation from a fully exposed emanating surface of a gel, comprising an open topped container having a perimeter defining an unobstructed opening from which the volatile products may be dispensed, said container having an annular attachment means, defining a plurality of interstices, disposed within the container adjacent the opening around the entire said perimeter thereof, said attachment means interstitially anchoring the gel around and adjacent said unobstructed opening of the container to define and sustain the emanating surface of the gel adjacent to the opening throughout the useful life of the dispenser, whereby during use, shrinkage of the gel will occur within the container as the gel within the container acts as a reservoir supplying the emanating surface wherein the attachment means is integrally formed with the container and comprises a plurality of flanges defining said interstices between the flanges and an adjacent wall portion of the dispenser adjacent the opening to captively engage the gel in the dispenser.

8. A dispenser according to claim 7 wherein the flanges extend longitudinally of the dispenser from the opening.

9. A dispenser according to claim 7 wherein the opening is circular and is defined by a cylindrical wall portion of the dispenser, the flanges being annular flanges in the wall portion adjacent the opening.

10. A process for providing a stable emanating surface of gel for the dispensation of volatile products therefrom comprising interstitially anchoring the gel to an annular structure surrounding the emanating surface, providing a reservoir of the gel to replenish and sustain the emanating surface, as said volatile products are dispensed throughout the useful life of the dispenser wherein the anchoring of the gel to a dispenser structure is achieved by allowing the gel in a liquified condition to penetrate the interstices of a porous band disposed about the emanating surface adjacent thereto and allowing the gel to solidify following said penetration.

11. A process according to claim 10 wherein said emanating surface initially is convex.

* * * * *